United States Patent
Edgington et al.

(10) Patent No.: US 12,042,299 B2
(45) Date of Patent: Jul. 23, 2024

(54) ELECTRONIC PATCH

(71) Applicant: AAG WEARABLE TECHNOLOGIES PTY LTD, Eagle Farm (AU)

(72) Inventors: Sean Edgington, Mount Martha (AU); Frank Baccalini, Keilor Downs (AU); Paul McCloskey, Los Angeles, CA (US)

(73) Assignee: AAG WEARABLE TECHNOLOGIES PTY LTD, Eagle Farm (AU)

( * ) Notice: Subject to any disclaimer, the term of this patent is extended or adjusted under 35 U.S.C. 154(b) by 914 days.

(21) Appl. No.: 17/052,769

(22) PCT Filed: May 3, 2018

(86) PCT No.: PCT/CN2018/085472
§ 371 (c)(1),
(2) Date: Nov. 3, 2020

(87) PCT Pub. No.: WO2019/210483
PCT Pub. Date: Nov. 7, 2019

(65) Prior Publication Data
US 2021/0236059 A1    Aug. 5, 2021

(51) Int. Cl.
*A61B 5/00* (2006.01)
*A61B 5/0205* (2006.01)
(Continued)

(52) U.S. Cl.
CPC ........ *A61B 5/6833* (2013.01); *A61B 5/02055* (2013.01); *A61B 5/0816* (2013.01);
(Continued)

(58) Field of Classification Search
CPC .............. A61B 5/6833; A61B 5/68335; A61B 5/02055; A61B 5/0816; A61B 5/14551;
(Continued)

(56) References Cited

U.S. PATENT DOCUMENTS

2007/0208262 A1    9/2007  Kovacs
2008/0139953 A1*   6/2008  Baker ................ A61B 5/14542
                                                    600/509
(Continued)

FOREIGN PATENT DOCUMENTS

CN    103445763 A  *  12/2013
CN    103445763 A     12/2013
WO    2019/210483 A1  11/2019

OTHER PUBLICATIONS

Patent Cooperation Treaty: International Preliminary Report on Patentability for PCT/CN2018/085472 dated Nov. 3, 2020; 5 pages.
(Continued)

*Primary Examiner* — Linda C Dvorak
*Assistant Examiner* — Abigail Bock
(74) *Attorney, Agent, or Firm* — Schwabe, Williamson & Wyatt, P.C.

(57) ABSTRACT

Provided herein is an electronic patch for applying to a wearable item. The electronic patch includes a sensor comprising a sensor pad and a sensor base that together define a stepped arrangement, an electrically conductive underlayer disposed under the sensor base, a circuit layer disposed under the underlayer and electrically coupled to the sensor via the underlayer, a first elastic layer overlying the sensor base and arranged adjacent the sensor pad, and a second elastic layer disposed under the circuit layer. Also provided is a wearable item that includes the aforementioned electronic patch as well as methods of making said wearable item and electronic patch.

19 Claims, 2 Drawing Sheets

(51) Int. Cl.
| | |
|---|---|
| *A61B 5/08* | (2006.01) |
| *A61B 5/1455* | (2006.01) |
| *C09J 5/06* | (2006.01) |
| *C09J 7/25* | (2018.01) |
| *C09J 7/40* | (2018.01) |
| *C09J 175/04* | (2006.01) |

(52) U.S. Cl.
CPC ...... *A61B 5/14551* (2013.01); *A61B 5/68335* (2017.08); *A61B 5/688* (2013.01); *C09J 5/06* (2013.01); *C09J 7/255* (2018.01); *C09J 7/40* (2018.01); *C09J 175/04* (2013.01); *A61B 2560/0412* (2013.01); *A61B 2562/14* (2013.01); *A61B 2562/164* (2013.01)

(58) Field of Classification Search
CPC ............ A61B 5/688; A61B 2560/0412; A61B 2562/14; A61B 2562/16; C09J 7/255; C09J 7/40; C09J 5/06; C09J 175/04
See application file for complete search history.

(56) References Cited

U.S. PATENT DOCUMENTS

| | | | |
|---|---|---|---|
| 2015/0157242 A1* | 6/2015 | Sabesan | A61B 5/6833 600/595 |
| 2016/0026213 A1* | 1/2016 | Li | G06F 1/163 361/679.03 |
| 2016/0324487 A1 | 11/2016 | Guo | |

OTHER PUBLICATIONS

Patent Cooperation Treaty: International Search Report and Written Opinion for PCT/CN2018/085472 dated Feb. 2, 2019; 7 pages.

\* cited by examiner

ELECTRONIC PATCH

CROSS-REFERENCE TO RELATED APPLICATION

The present application is a national phase entry under 35 U.S.C. § 371 of International Application No. PCT/CN2018/085472, filed May 3, 2018, which designates the United States of America, the entire disclosure of which is hereby incorporated by reference and for all purposes.

FIELD OF THE INVENTION

This invention relates to an electronic patch for applying to a wearable item. In particular, the invention relates to an electronic patch for applying to a wearable item for detecting a physiological parameter of a user or wearer of the wearable item. Additionally, the present invention relates to products, such as wearable items, containing the electronic patch and methods of making same.

BACKGROUND TO THE INVENTION

A wearable patch is an electronic patch that can be applied to, for example, clothing so as to be worn by a user and contact the user's skin and operate for an extended period of time from hours to months. In this manner, an electronic patch can be integrated with different sensors so as to monitor one or more physiological parameters, such as vital signs, motion tracking, heart rate and rhythm (e.g., ECG) and skin temperature, of a user.

Such wearable conductive materials are generally not sufficiently durable and stretchable and therefore can deteriorate rapidly so as to effectively lose their conductive properties with, for example, repeated elongations during body movements and laundering. Under stress, different layers in wearable patches can break or delaminate rendering the wearable patches inoperable. Additionally, wearable electronic patches, depending upon their component materials, typically can only be applied to a limited range of fabric types. Furthermore, a wearable electronic patch often includes multiple rigid layers to provide sensor, computation, and communication functions, which leads to user discomfort when they wear such wearable electronic patches.

Therefore, there is a strong need for an electronic patch for application to a wearable item that overcomes one or more of the aforementioned issues.

SUMMARY OF THE INVENTION

The present invention is directed to an electronic patch and methods of making same. Additionally, the present invention is directed to a wearable item including the electronic patch and methods of making same.

In a first aspect, the invention provides an electronic patch for applying to a wearable item, the electronic patch comprising:
- a sensor comprising a sensor pad and a sensor base, the sensor base disposed under the sensor pad and extending inwardly therefrom so as to define a stepped arrangement, the sensor pad adapted to detect a first physiological parameter upon contact with a user's skin;
- an electrically conductive underlayer disposed under the sensor base and electrically coupled thereto;
- a circuit layer disposed under the underlayer and electrically coupled to the sensor via the underlayer;
- a first elastic layer overlying at least a portion of the sensor base and arranged so as to be disposed adjacent the sensor pad and extending therearound; and
- a second elastic layer disposed under the circuit layer.

In one embodiment, the electronic patch further comprises:
- an outer adhesive layer disposed on an upper surface of the first elastic layer, and
- a release film disposed on a side of the outer adhesive layer and extending over the sensor pad.

In particular embodiments, the electronic patch further comprises an inner adhesive layer disposed under the second elastic layer and configured to adhere to the wearable item.

The electronic patch of the present aspect suitably further comprises:
- a further sensor arranged in a spaced apart relationship with respect to the sensor and comprising a further sensor pad and a further sensor base, the further sensor base disposed under the further sensor pad and extending inwardly therefrom so as to define a stepped arrangement, the further sensor pad adapted to detect a second physiological parameter upon contact with a user's skin;
- an electrically conductive further underlayer disposed under the further sensor base and electrically coupled thereto;
- a further circuit layer disposed under the further underlayer and electrically coupled to the further sensor via the further underlayer;
- the first elastic layer overlying at least a portion of the further sensor base and arranged so as to be disposed adjacent the further sensor pad and extending therearound; and
- the second elastic layer disposed under the further circuit layer.

In one embodiment, the sensor and the further sensor comprise or are formed from a silver paste.

In one embodiment, the underlayer and the further underlayer comprise or are formed from a carbon paste.

In particular embodiments, the circuit layer and the further circuit layer comprise or are formed from a silver paste.

Suitably, the first and/or second elastic layers comprise a material selected from the group consisting of a tris(2-methyl-1-aziridinepropionate) derivative, a polyurethane and any combination thereof. Preferably, the tris(2-methyl-1-aziridinepropionate) derivative is or comprises trimethylolpropane tris(2-methyl-1-aziridinepropionate).

In one embodiment, the outer adhesive layer comprises a first adhesive agent containing a polyurethane, a polyester, an ethylene-vinyl acetate copolymer and/or a polyamide.

In certain embodiments, the inner adhesive layer comprises:
- a first portion comprising a second adhesive agent containing a hot melt adhesive agent, and
- a second portion comprising a third adhesive agent containing a polyurethane, a polyester and/or a polyamide.

Suitably, the electronic patch of the present aspect is formed at least in part by a screen printing process.

Suitably, the physiological parameter is selected from the group consisting of a blood pulse characteristic, blood pressure, heart rate, temperature, position, a blood oxygen level, a blood carbon dioxide level, respiration rate, muscle activity and any combination thereof.

In a second aspect, the invention provides a method of producing an electronic patch, including the steps of:
(a) depositing a first elastic layer so as to define a space to receive a sensor pad adjacent thereto;
(b) depositing the sensor pad adjacent the first elastic layer;
(c) depositing a sensor base so as to underlie the sensor pad and the first elastic layer, and wherein the sensor base and the sensor pad define a stepped arrangement;
(d) depositing an electrically conductive underlayer to underlie the sensor base;
(e) depositing a circuit layer to underlie the underlayer; and
(f) depositing a second elastic layer to underlie the circuit layer.

Suitably, the method of the present aspect further includes the step of:
(g) depositing an inner adhesive layer to underlie the second elastic layer.

In other embodiments, the present method further includes the initial step of depositing an outer adhesive layer on a release film, the outer adhesive layer to overlie at least a portion of the first elastic layer.

In one embodiment, one or more of the depositing steps are performed at least in part by a screen printing process.

Suitably, the electronic patch is that of the aforementioned aspect.

In a third aspect, the invention provides a wearable item comprising an electronic patch adhered thereto, wherein the electronic patch is that of the first aspect.

Suitably, the wearable item further comprises a monitoring device electrically coupled to the electronic patch. Preferably, the monitoring device is electrically coupled to the electronic patch by one or more electrodes extending therethrough. With respect to the present embodiment, the electronic patch preferably further comprises a cover element extending over an outer surface of the electrodes so as to prevent their contact with a user's skin.

In a fourth aspect, the invention provides a method of producing a wearable item comprising an electronic patch adhered thereto, including the steps of:
(a) contacting the electronic patch of the first aspect to a portion of the wearable item;
(b) applying heat to the electronic patch and/or the wearable item so as to adhere the electronic patch to the wearable item.

Suitably, the present method further includes the initial step of removing a release film from the electronic patch.

In one embodiment, the method further includes the step of engaging one or more electrodes with the electronic patch.

The method of the present aspect suitably further includes the step of electrically coupling a monitoring device to the electronic patch.

As used herein, except where the context requires otherwise, the term "comprise" and variations of the term, such as "comprising", "comprises" and "comprised", are not intended to exclude further elements, components, integers or steps but may include one or more unstated further elements, components, integers or steps.

In this specification, adjectives such as first and second, top and bottom, upwards and downwards, and the like may be used solely to distinguish one element or action from another element or action without necessarily requiring or implying any actual such relationship, hierarchy or order.

It will be appreciated that the indefinite articles "a" and "an" are not to be read as singular indefinite articles or as otherwise excluding more than one or more than a single subject to which the indefinite article refers. For example, "a" sensor includes one sensor, one or more sensors and a plurality of sensors.

DETAILED DESCRIPTION OF THE INVENTION

The present invention is predicated, at least in part, on the surprising discovery that a specifically designed electronic patch for applying to a fabric resulted in significant improvements in wash resistance, stretchability, flexibility and ease of mass production. In addition to this, this electronic patch has been found to capable of being successfully applied to a broad range of fabrics or textiles with ease. Accordingly, in some embodiments, the present invention aims to overcome the drawbacks in prior art electronic patches so as to provide, highly stretchable, compliant, durable and/or comfortable wearable electronic patches whilst adequately performing intended sensing and communication functions at and away from a user's skin to which the electronic patch is applied or contacted.

Accordingly, in one aspect, the invention provides an electronic patch for applying to a wearable item, the electronic patch comprising:
a sensor comprising a sensor pad and a sensor base, the sensor base disposed under the sensor pad and extending inwardly therefrom so as to define a stepped arrangement, the sensor pad adapted to detect a first physiological parameter upon contact with a user's skin;
an electrically conductive underlayer disposed under the sensor base and electrically coupled thereto;
a circuit layer disposed under the underlayer and electrically coupled to the sensor via the underlayer;
a first elastic layer overlying at least a portion of the sensor base and arranged so as to be disposed adjacent the sensor pad and extending therearound; and
a second elastic layer disposed under the circuit layer.

As provided herein, the term "wearable item" refers to all clothing items and accessories that can be worn physically on a user. Examples of wearable items include, but are not limited, to clothes such as shirts, pants, coats, undergarments, shorts, tops, t-shirts, sweatshirts, sweaters, jackets, windbreakers, uniforms and sportswear. Additional examples of wearable items include but are not limited to hats, wigs, glasses, sunglasses, watches, head bands, shoes, socks, belts, ties and the like.

In particular embodiments, the electronic patch is for applying or adhering to a fabric substrate of the wearable item. The fabric substrate may be or comprise any suitable natural or synthetic fabric as are known in the art, including woven, non-woven and knit fabrics. By way of example, the fabric substrate may be selected from the group consisting of cotton, wool, silk, hemp, polyester, polypropylene, spandex, nylon and any combination thereof.

As used herein, the term "electronic patch" refers to a device, in the form of a topical electronic patch, that may include sensors for sensing or measuring one or more detectable physiological parameters or characteristics. A wearable electronic patch may be configured to transmit signals indicative of a measurement or sensed state, condition, or quantity of the one or more detectable physiological parameters.

By "sensor" is meant a device that is configured to detect or measure a physiological parameter and records, generates signals, or otherwise responds to the physiological parameter.

As used herein, "electrically coupled" refers to a relationship between structures or regions, such as a sensor and an associated underlayer, that allows electrical current to flow at least partially between them so as to define a continuously conductive pathway. This definition is intended to include aspects where the structures are in physical contact and those aspects where the structures are not in physical contact.

"Electrically conductive" describes a material that has the capacity for electron conduction, hole conduction, or the ability to otherwise undergo charge transfer.

The term "circuit" refers to any type of electrical circuit, including a circuit that serves as an antenna, and combinations of electrical circuits and/or antennas.

In one embodiment, the electronic patch further comprises:
an outer adhesive layer disposed on an upper surface of the first elastic layer, and
a release film disposed on a side of the outer adhesive layer and extending over the sensor pad.

In particular embodiments, the electronic patch further comprises an inner adhesive layer disposed under the second elastic layer and configured to adhere to the wearable item.

The electronic patch of the present aspect suitably further comprises:
a further sensor arranged in a spaced apart relationship with respect to the sensor and comprising a further sensor pad and a further sensor base, the further sensor base disposed under the further sensor pad and extending inwardly therefrom so as to define a stepped arrangement, the further sensor pad adapted to detect a second physiological parameter upon contact with a user's skin;
an electrically conductive further underlayer disposed under the further sensor base and electrically coupled thereto;
a further circuit layer disposed under the further underlayer and electrically coupled to the further sensor via the further underlayer;
the first elastic layer overlying at least a portion of the further sensor base and arranged so as to be disposed adjacent the further sensor pad and extending therearound; and
the second elastic layer disposed under the further circuit layer.

In one embodiment, the sensor and the further sensor comprise or are formed from a silver paste. In this regard, it was found that the sensor and/or further sensor should preferably contain silver particles in an elastic or flexible polymer based binder such as a fluorinated polymer. As described in more detail in Example 1, the silver paste can be applied, for example, on a release film by screen printing. The silver paste forms an elastic path, where the silver particles are at least partially responsible for the electric conductivity of the path. As an alternative to silver paste, it may also be possible to use some inks and/or pastes based on copper compounds or carbon-based materials, such as carbon flakes, or aluminum based pastes, according to the desired result.

In one embodiment, the underlayer and the further underlayer comprise or are formed from a carbon paste. The carbon paste preferably contains carbon particles, inclusive of nanoparticles, in an elastic or flexible polymer based binder, such as a polyurethane, so as to impart a desired level of elasticity to the underlayer and further underlayer. In this manner, the carbon paste can facilitate electrical conduction of electrical detection signals from the sensor and the further sensor upon detection of a physiological parameter thereby and improve the electrical conductive properties thereof, whilst also being able to be stretched during use.

In particular embodiments, the circuit layer and the further circuit layer comprise or are formed from a silver paste, such as that hereinbefore described.

The first and second elastic layers suitably allow for the sensor, the further sensor, the underlayer, the further underlayer, the circuit layer and/or the further circuit layer to be elongated and stretched without comprising the integrity (e.g., cracking) and functionality of these layers disposed therebetween. The first and second layers also preferably facilitate recovery of the electronic patch from a flexed position to an unflexed position. Suitably, the first and/or second elastic layers comprise a material selected from the group consisting of a tris(2-methyl-1-aziridinepropionate) derivative, a polyurethane and any combination thereof. Preferably, the tris(2-methyl-1-aziridinepropionate) derivative is or comprises trimethylolpropane tris(2-methyl-1-aziridinepropionate).

In one embodiment, the outer adhesive layer comprises a first adhesive agent containing a polyurethane, a polyester, an ethylene-vinyl acetate copolymer and/or a polyamide, inclusive of solutions, emulsions, suspensions, pastes, and the like, thereof.

In certain embodiments, the inner adhesive layer comprises:
a first portion comprising a second adhesive agent containing a hot melt adhesive agent, and
a second portion comprising a third adhesive agent containing a polyurethane, a polyester and/or a polyamide.

Preferably, the second adhesive agent contains a powdered hot melt adhesive agent.

It will be appreciated that the third adhesive agent may be in any suitable form, such as, but not limited to solutions, emulsions, suspensions, pastes, and the like, as are known in the art.

Suitably, the inner adhesive layer is configured for binding or adhering to a fabric substrate, such as that hereinbefore described. It is this combination of the second and third adhesive agents of the inner adhesive layer that the inventors have found contributes to the durability of the electronic patch described herein.

Suitably, the electronic patch of the present aspect is formed at least in part by a screen printing process.

Accordingly, in particular embodiments, the circuit layer comprises a printed circuit. It will be appreciated that printed circuits may include one or more layers of insulating material on which a plurality of tracks of conductive material are laid. Alternatively, a printed circuit can be made of a conductive material, with a laminar structure which is laid like a carpet. The circuit layer of the present invention can be manufactured by engraving and/or deposition or pressing.

The term "physiological parameter" refers to any variable parameter which is measurable or calculable and is representative of a physiological activity. By way of example, a physiological parameter can include a blood pulse characteristic, blood pressure, heart rate, temperature, position, a blood oxygen level, a blood carbon dioxide level, respiration rate, muscle activity and any combination thereof. The physiological parameter can be a time-related parameter, an amplitude-related parameter or any combination thereof.

In preferred embodiments, the physiological parameter is selected from the group consisting of a blood pulse characteristic, blood pressure, heart rate, temperature, position, a blood oxygen level, a blood carbon dioxide level, respiration rate, muscle activity and any combination thereof.

Figure 1:
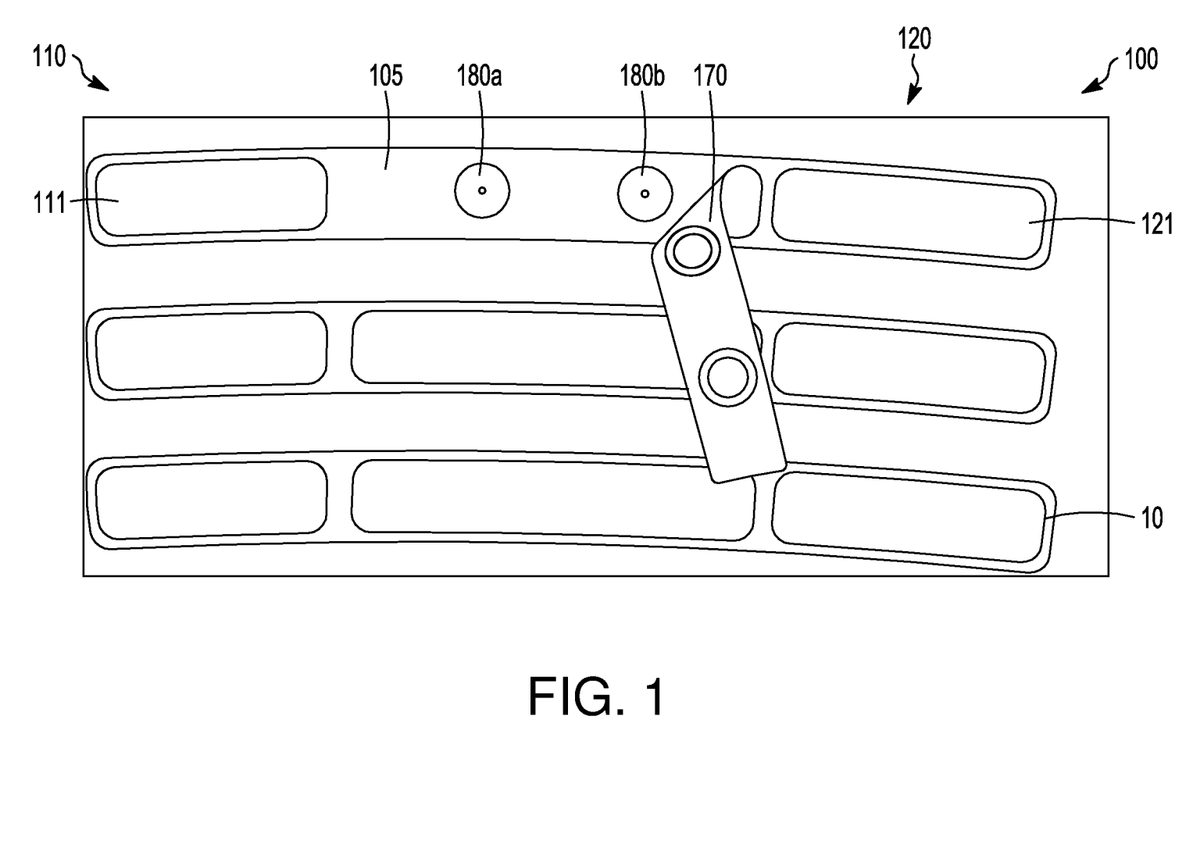
FIG. 1 provides a perspective view of an embodiment of an electronic patch of the invention as applied to a wearable item.
Figure 2:
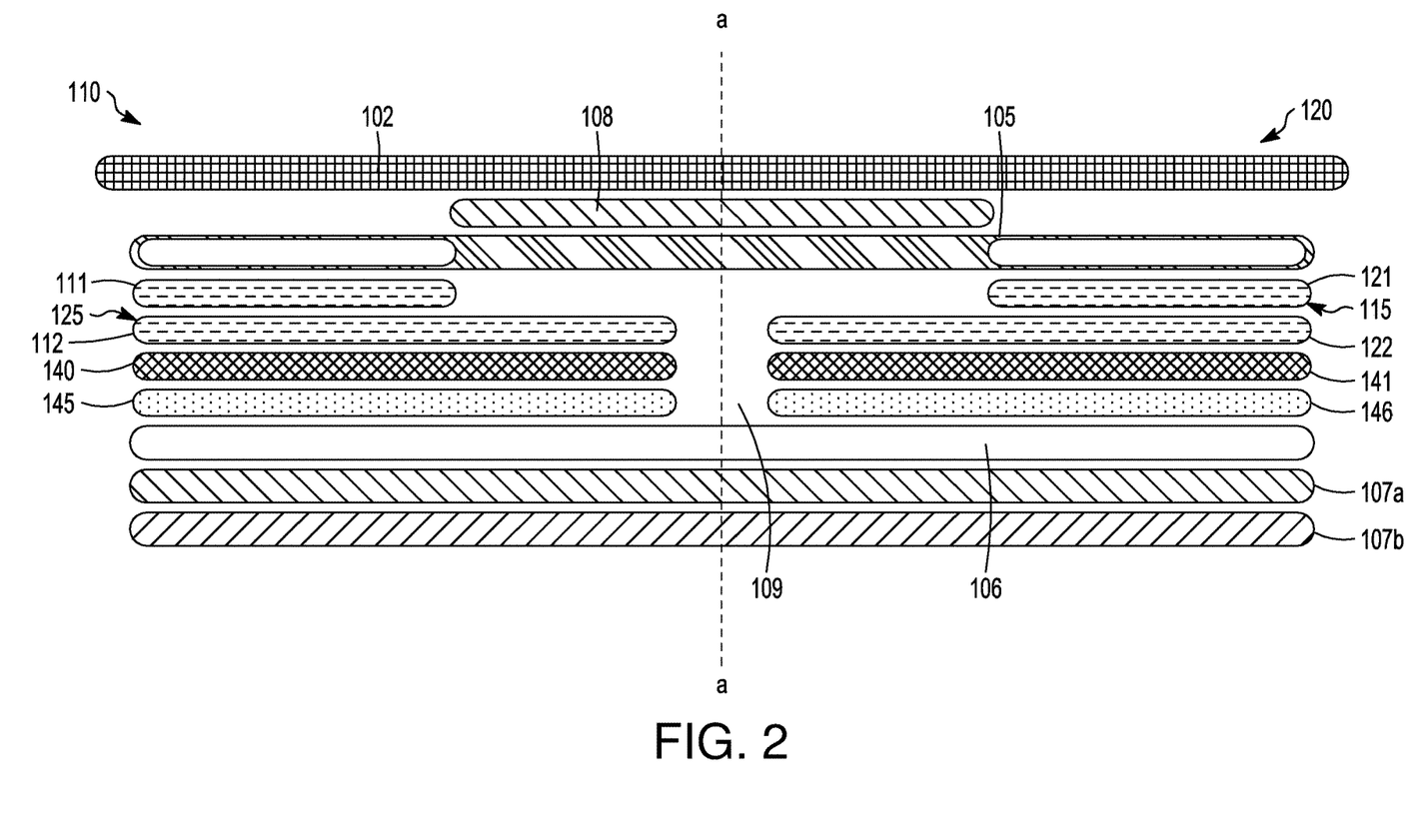
FIG. 2 illustrates a longitudinal cross-sectional schematic view of the electronic patch of FIG. 1.

Referring to FIGS. 1 and 2, an embodiment of an electronic patch 100 of the invention is provided. The electronic patch 100 defines a central axis or plane a and has first and second sensors 110,120 disposed either side thereof that extend radially outward in opposite directions therefrom. It will be apparent to the skilled person that the first and second sensors 110,120 may comprise any suitable conductive material known in the art, such as, but not limited to, particles or flakes of copper, silver, carbon, and/or aluminium.

The first and second sensors 110,120 include respective first and second conductive sensor pads 111,121 that define a first sensor layer 115. Preferably, the first sensor layer 115 is wash fast and durable, owing to it being required to contact a user's skin directly. As can be seen from FIG. 1, the first sensor pad 111 and the second sensor pad 121 are spaced apart so as to be disposed on opposite end portions of the three-dimensional electronic patch 100.

Underlying their respective first and second sensor pads 111,121, are electrically conductive first and second sensor bases 112,122. As can be observed from FIG. 2, each of the first and second sensor bases 112,122 substantially underlie their respective sensor pad 111, 121 and extend centrally or inwardly therefrom so as to define a stepped arrangement. In addition to this, the first and second sensor bases 112,122 define a second sensor layer 125. In the embodiment provided, each of the first and second sensor pads 111,121 and the first and second sensor bases 112,122 are formed from a silver-based paste.

As illustrated in FIGS. 1 and 2, the electronic patch 100 further includes an outer first elastic layer 105 overlying and disposed proximate an outer surface of both the first and second sensor bases 112,122 and extending therebetween. The first elastic layer 105 is further arranged so as to be disposed adjacent and extend circumferentially around side portions of both of the first and second sensor pads 111,121. By virtue of this arrangement, it is only an outer surface of each of the first and second sensor pads 111,121 of the first and second sensors 110,120 that is capable of contacting a user's skin during use.

Disposed directly underneath each of the first and second sensor bases 112,122 and electrically coupled thereto are respective and opposed first and second underlayers 140, 141. In this manner, the first and second underlayers 140,141 are electrically conductive and may comprise any conductive material known in the art, such as, but not limited to, particles or flakes of copper, silver, carbon, and/or aluminium. In the embodiment provided, the first and second underlayers 140,141 are each formed from a carbon-based paste.

Similar to the above, the electronic patch 100 further includes spaced apart first and second circuit layers 145,146 that are disposed under and proximate the respective first and second underlayers 140,141 and electrically coupled thereto. By virtue of this arrangement, the first and second circuit layers 145,146 are also electrically coupled to the first and second sensors 110,120 respectively by way of the respective first and second underlayers 140,141. Similar to the above, the first and second circuit layers 145,146 can comprise any conductive material known in the art, such as those hereinbefore described. In the present embodiment, each of the first and second circuit layers 145,146 are formed from a silver based paste. As can be observed in FIG. 2, the respective sensor bases 112,122, the respective underlayers 140,141 and the respective circuit layers 145,146 are spaced apart at respective end portions of the electronic patch 100 so as to define a central space 109 therebetween. To this end, the central space 109 provides physical separation or a spacing region between the first sensor 110 and the second sensor 120 as well as electrical detection signals respectively derived therefrom.

Disposed directly underneath the first and second circuit layers 145,146 and extending therebetween to enclose the central space 109 is a second elastic layer 106. The flexibility or stretchability of the second elastic layer 106 allows for the first and second sensor layers 115,125, the underlayers 140,141 and/or the circuit layers 145,146 to be elongated, such as during use, whilst preventing or minimising any damage or cracking to these layers so as to maintain their conductivity over time and repeated use.

As can be seen from FIG. 2, the electronic patch 100 further includes first and second inner adhesive layers 107a,b disposed under the second elastic layer 106. In the embodiment provided, the first inner adhesive layer 107a comprises an elastic and liquid-based adhesive agent (e.g., a polyurethane solution in a Cellosolve acetate (CAC) solvent), which may be any appropriate adhesive agent known in the art. Additionally, the second inner adhesive layer 107b preferably comprises a powdered hot melt adhesive agent. Preferably, the powdered hot melt adhesive agent of the second inner adhesive layer 107a is added to the first inner adhesive layer whilst it is still wet or moist and prior to drying.

By virtue of this arrangement, the first and second inner adhesive layers 107a,b are configured to adhere to a wearable item upon the application of heat thereto and provide durability to the bond therebetween. To this end, the electronic patch 100 is preferably durable enough to withstand 50 or more (e.g., 50, 60, 70, 80, 90, 100 or any range therein), and even more preferably, 100 or more (e.g., 100, 110, 120, 130, 140, 150, 160, 170, 180, 190, 200 or any range therein) wash cycles, before, for example, any delamination of the aforementioned layers is observed.

For production and storage purposes prior to application to a wearable item, the electronic patch 100 further includes an outer release film 102. As shown in FIG. 2, the release film 102 is adhered to an outer surface of the first elastic layer 105 by way of an outer adhesive layer 108 disposed therebetween. As will be understood, the outer adhesive layer 108 may comprise any suitable adhesive agent known in the art, such as a polyurethane-based solution. In addition to retaining the release film 102 in a desired position, the outer adhesive layer 108 can also function to receive and retain one or more cover elements 170, as shown in FIG. 1, once the release film 102 has been removed from the electronic patch 100. In this regard, the cover elements 170 can be adhered to the outer adhesive layer 108 before or after application of the electronic patch 100 to the wearable item 10.

Each of the first and second sensors 110,120 are capable of producing an electrical detection signal upon detection of a physiological parameter upon contact with a user's skin. It will be appreciated that each of the first and second sensors 110,120 can be configured to sense or detect the same or different physiological parameters. By way of example, both of the first and second sensors 110,120 can be operable to determine skin temperature, whilst in an alternative embodiment, the first sensor 110 can be configured to measure skin temperature and the second sensor 120 can be configured to determine the heart rate of a user. In the embodiment provided, the first and second sensors 110,120 are configured to detect a measure of skin temperature upon contact with a user's skin.

Once detected by the first and/or second sensor 110,120, the electrical detection signal is then conducted through its respective underlayer 140,141 to the underlying circuit layer 145,146. As shown in FIG. 1, the electronic patch 100 further includes a pair of electrodes 180a,b in the form of press studs or conductive pins extending therethrough. In this manner, the first electrode 180a extends through the first elastic layer 105, the first sensor base 112, the first underlayer 140, the first circuit layer 145, the second elastic layer 106, the first and second inner adhesive layers 107a,b and the wearable item 10. Conversely, the second electrode 180b extends through the first elastic layer 105, the second sensor base 122, the second underlayer 141, the second circuit layer 146, the second elastic layer 106, the first and second inner adhesive layers 107a,b and the wearable item 10. Accordingly, each of the first and second electrodes 180a,b are capable of conducting separate electrical detection signals derived from the respective first and second sensors 110,120.

In view of the above, the first and second electrodes 180a,b are preferably positioned subsequent to the electronic patch 100 being applied to the wearable item 10. The cover element 170 is then applied over and across the first and second electrodes 180a,b so as to prevent contact with a user's skin when the electronic patch 100 is in use. As per FIG. 1, it will be appreciated that the cover element 170 has been largely removed or delaminated so as to illustrate the first and second electrodes 180a,b positioned thereunder. During use, however, the first and second electrodes 180a,b will be covered by the cover element 170 so as to prevent their contact with a user's skin.

Although not shown in FIG. 1, the first and second electrodes 180a,b are adapted to be electrically coupled or engaged to a monitoring or recordal device (not shown) in a permanent or reversible fashion. Accordingly, the monitoring device (not shown) is electrically coupled to the first and second sensors 110,120 via the first and second electrodes 180a,b.

It is envisaged that the monitoring device may be any as are commonly known in the art.

In a further aspect, the invention provides a method of producing an electronic patch, including the steps of:
(a) depositing a first elastic layer so as to define a space to receive a sensor pad adjacent thereto;
(b) depositing the sensor pad adjacent the first elastic layer;
(c) depositing a sensor base so as to underlie the sensor pad and the first elastic layer, and wherein the sensor base and the sensor pad define a stepped arrangement;
(d) depositing an electrically conductive underlayer to underlie the sensor base;
(e) depositing a circuit layer to underlie the underlayer; and
(f) depositing a second elastic layer to underlie the circuit layer.

Suitably, the method of the present aspect further includes the step of:
(g) depositing an inner adhesive layer to underlie the second elastic layer.

The present method suitably further includes the initial step of depositing an outer adhesive layer on a release film, the outer adhesive layer to overlie at least a portion of the first elastic layer. In this regard, the release film may comprise any suitable material, such as polymeric plastic materials as are known in the art (e.g., polyethylene terephthalate).

In one embodiment, one or more of the depositing steps are performed at least in part by a screen printing process, such as that described in Example 1 below.

The skilled artisan will understand screen printing to generally describe a process wherein a squeegee or blade is used to apply force or pass liquid or semi-liquid material, such as ink, adhesives, conductive pastes and the like, through a mesh which has areas of the mesh blocked in a patternwise fashion so that the ink is transferred through the mesh to an underlying substrate which forms a negative of the blocked pattern on the mesh.

Suitably, the electronic patch is that of the aforementioned aspect.

In a related aspect, the invention provides a wearable item comprising an electronic patch adhered thereto, wherein the electronic patch is that of the first mentioned aspect.

Suitably, the wearable item further comprises a monitoring device electrically coupled to the electronic patch. Preferably, the monitoring device is electrically coupled to the electronic patch by one or more electrodes extending therethrough. With respect to the present embodiment, the electronic patch preferably further comprises a cover element extending over an outer surface of the electrodes so as to prevent their contact with a user's skin.

In another aspect, the invention provides a method of producing a wearable item comprising an electronic patch adhered thereto, including the steps of:
(a) contacting the electronic patch of the first mentioned aspect to a portion of the wearable item;
(b) applying heat to the electronic patch and/or the wearable item so as to adhere the electronic patch to the wearable item.

Suitably, the present method further includes the initial step of removing a release film from the electronic patch.

In one embodiment, the method further includes the step of engaging one or more electrodes with the electronic patch.

The method of the present aspect suitably further includes the step of electrically coupling a monitoring device to the electronic patch.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

Any reference to publications cited in this specification is not an admission that the disclosures constitute common general knowledge in Australia or any other jurisdiction.

In order that the invention may be more readily understood and put into practice, one or more preferred embodiments thereof will now be described, by way of example only.

EXAMPLES

Example 1

An embodiment of a method of forming or producing an embodiment of the electronic patch 100 is provided in Example 1. It will be appreciated that the electronic patch described herein may be produced by any method known in the art and more preferably by way of printed electronics. Printed electronics is a relatively new technology that prints conductive and semi-conducting elements using a simple and commonly used printing equipment such as inkjet, screen printing, flexography, gravure, and offset lithography on a common media such as paper, polymers, plastic and textiles. In one particular embodiment, one or more component layers of the electronic patch are formed by screen printing.

In the present example, the electronic patch 100 is formed by a screen printing process outlined below. Table 1 provides the component layers of the electronic device 100, as well as their component material therein.

| Layer | Component printed layers | Material |
| --- | --- | --- |
| Cover layer | 1 | Matt polyethylene terephthalate (PET) |
| Outer adhesive layer | 6 | Polyurethane solution in a Cellosolve acetate (CAC) solvent |
| First elastic layer (coloured) | 6 | trimethylolpropane tris(2-methyl-1-aziridinepropionate) |
| First sensor layer | 2 | Silver paste including silver powder, 2-(2-Ethoxyethoxy)ethyl acetate, fluorinated polymer and triethyl phosphate |
| Second sensor layer | 1 | Same as for the first sensor layer |
| Conductive underlayer | 1 | Carbon paste including carbon powder and (2-methoxymethylethoxy)propanol |
| Circuit layer | 2 | Silver paste including silver powder |
| Second elastic layer | 6 | Polyurethane in cyclohexanone |
| First inner adhesive layer | 6 | Polyurethane solution in a CAC solvent |
| Second inner adhesive layer | 1 | Hot melt powdered thermoplastic aromatic polyurethane, fully reacted |

Screen Preparation
Screens for glue and colour are set up as follows:
Mesh Type=X
Mesh Count=156
Tension=23N±2
Set Angle=90°
Emulsion coating thickness=110 mu
Screens for conductive pastes are set up as follows:
Mesh Type=X
Mesh Count=175
Tension=23N±2
Set Angle=30°
Emulsion coating thickness=105 mu
The screens are dried over night @ 60°
They are then exposed to Halogen 1500 w light for 5 minutes with the desired pattern vacuumed onto the bottom of the screen in reverse. Then washed out in cold water for 10 min. They are then left to dry overnight at 60°. They are now ready for use.

The screens are placed into the printing machine and securely fastened, then adjusted into registration. The squeegee is fitted in on a 40° angle and secured. The squeegee rubber is 75PO and speed set at medium (7) with the flood bar set at fast (9).
Change Screen
Each time there is an artwork/screen change the machine needs to be set up at the same settings:
0 PET RELEASE FILM
1 GLUE×6
2 COLOUR×6
3 SENSOR×2
4 SENSOR×1
CARBON×2
6 SILVER×2
7 CLEAR×6
8 GLUE×6
9 POWDER GLUE
0 Pet Release Film
The PET release film is 1.0 mm thick and pre shrunk through tunnel dryer at 120° for 90 seconds and cooled prior to use.
1 Glue×6 Change Screen
The Glue Layer is printed six times and each layer is dried through the tunnel dryer at 80° for 50 seconds then 20 seconds through the cooling tunnel. The drying process is repeated twice for each layer.
2 Colour×6 Change Screen
The Colour Layer is printed six times and each layer is dried through the tunnel dryer at 80° for 50 seconds then 20 seconds through the cooling tunnel. The drying process is repeated twice for each layer.
6 Silver×2
The Silver Layer is printed two times and each layer is dried through the tunnel dryer at 80° for 50 seconds then 20 seconds through the cooling tunnel. The drying process is repeated twice for each layer.
7 Clear×6 Change Screen
The Clear Layer is printed six times and each layer is dried through the tunnel dryer at 80° for 50 seconds then 20 seconds through the cooling tunnel. The drying process is repeated twice for each layer.
8 Glue×6 Change Screen
The Glue Layer is printed five times and each layer is dried through the tunnel dryer at 80° for 50 seconds then 20 seconds through the cooling tunnel. The drying process is repeated twice for each layer.
9 Powder Glue
The last Glue Layer is printed and while still wet it is put through the Glue Powdering machine and then stacked on a rack. This rack is dried in an oven at 80° for 30 minutes. Then each sheet is tunnel dried at 150° for 100 seconds.
The conductive heat transfer is now completed and ready for transferring onto the fabric. The position of the conductive transfer is aligned by a cross hair laser and then pressed into place using the following technique:
Heat Press Settings:
TEMP=160°
Time=5 seconds first press
Time=15 seconds second press
Time=5 seconds third press
Pressure=2.75 PSI
$1^{st}$ Press the fabric to remove any moisture
Place transfer in position
$2^{nd}$ Press
Remove the PET layer
$3^{rd}$ Press

The invention claimed is:

1. An electronic patch for applying to a wearable item, the electronic patch comprising:
 a sensor comprising a sensor pad and a sensor base, the sensor base disposed under the sensor pad and extending inwardly therefrom so as to define a stepped arrangement, the sensor pad adapted to detect a first physiological parameter upon contact with a user's skin;
 an electrically conductive underlayer disposed under the sensor base and electrically coupled thereto;
 a circuit layer disposed under the underlayer and electrically coupled to the sensor via the underlayer;
 a first elastic layer overlying at least a portion of the sensor base and arranged so as to be disposed adjacent the sensor pad and extending therearound; and
 a second elastic layer disposed under the circuit layer; and
 an inner adhesive layer disposed under the second elastic layer and configured to adhere to the wearable item;
 wherein the inner adhesive layer comprises:
  a first portion comprising a second adhesive agent containing a hot melt adhesive agent, and
  a second portion comprising a third adhesive agent containing a polyurethane, a polyester or a polyamide.

2. The electronic patch of claim 1, further comprising:
 an outer adhesive layer disposed on an upper surface of the first elastic layer, and
 a release film disposed on a side of the outer adhesive layer and extending over the sensor pad.

3. The electronic patch of claim 2, wherein the outer adhesive layer comprises a first adhesive agent containing a polyurethane, a polyester, an ethylene-vinyl acetate copolymer or a polyamide.

4. The electronic patch of claim 1, further comprising:
 a further sensor arranged in a spaced apart relationship with respect to the sensor and comprising a further sensor pad and a further sensor base, the further sensor base disposed under the further sensor pad and extending inwardly therefrom so as to define a stepped arrangement, the further sensor pad adapted to detect a second physiological parameter upon contact with a user's skin;
 an electrically conductive further underlayer disposed under the further sensor base and electrically coupled thereto;
 a further circuit layer disposed under the further underlayer and electrically coupled to the further sensor via the further underlayer;
 the first elastic layer overlying at least a portion of the further sensor base and arranged so as to be disposed adjacent the further sensor pad and extending therearound; and
 the second elastic layer disposed under the further circuit layer.

5. The electronic patch of claim 4, wherein:
 the sensor and the further sensor comprise or are formed from a silver paste; or
 the underlayer and the further underlayer comprise or are formed from a carbon paste; or
 the circuit layer and the further circuit layer comprise or are formed from a silver paste.

6. The electronic patch of claim 1, wherein the first or second elastic layers comprise a material selected from the group consisting of a tris(2-methyl-1-aziridinepropionate) derivative, a polyurethane and any combination thereof.

7. The electronic patch of claim 6, wherein the tris(2-methyl-1-aziridinepropionate) derivative is or comprises trimethylolpropane tris(2-methyl-1-aziridinepropionate).

8. The electronic patch of claim 1, formed at least in part by a screen printing process.

9. The electronic patch of claim 1, wherein the physiological parameter is selected from the group consisting of a blood pulse characteristic, blood pressure, heart rate, temperature, position, a blood oxygen level, a blood carbon dioxide level, respiration rate, muscle activity and any combination thereof.

10. A wearable item comprising an electronic patch adhered thereto, wherein the electronic patch is that of claim 1.

11. The wearable item of claim 10, further comprising a monitoring device electrically coupled to the electronic patch.

12. The wearable item of claim 11, wherein the monitoring device is electrically coupled to the electronic patch by one or more electrodes extending therethrough.

13. The wearable item of claim 12, further comprising a cover element extending over an outer surface of the electrodes so as to prevent their contact with a user's skin.

14. A method of producing a wearable item comprising an electronic patch adhered thereto, including the steps of:
 (a) contacting the electronic patch of claim 1 to a portion of the wearable item;
 (b) applying heat to the electronic patch and/or the wearable item so as to adhere the electronic patch to the wearable item.

15. The method of claim 14, further including the initial step of removing the release film from the electronic patch;
 and optionally further including the step of engaging one or more electrodes with the electronic patch;
 and optionally further including the step of electrically coupling a monitoring device to the electronic patch.

16. A method of producing an electronic patch, including the steps of:
 (a) depositing a first elastic layer so as to define a space to receive a sensor pad adjacent thereto;
 (b) depositing the sensor pad adjacent the first elastic layer;
 (c) depositing a sensor base so as to underlie the sensor pad and the first elastic layer, and wherein the sensor base and the sensor pad define a stepped arrangement;
 (d) depositing an electrically conductive underlayer to underlie the sensor base;
 (e) depositing a circuit layer to underlie the underlayer;
 (f) depositing a second elastic layer to underlie the circuit layer; and
 (g) depositing an inner adhesive layer to underlie the second elastic layer;
 wherein the inner adhesive layer comprises:
  a first portion comprising a second adhesive agent containing a hot melt adhesive agent, and
  a second portion comprising a third adhesive agent containing a polyurethane, a polyester or a polyamide.

17. The method of claim 16, further including the initial step of depositing an outer adhesive layer on a release film, the outer adhesive layer to overlie at least a portion of the first elastic layer.

18. The method of claim 16, wherein one or more of the depositing steps are performed at least in part by a screen printing process.

19. The method of claim 16, wherein the electronic patch comprises:
- a sensor comprising a sensor pad and a sensor base, the sensor base disposed under the sensor pad and extending inwardly therefrom so as to define a stepped arrangement, the sensor pad adapted to detect a first physiological parameter upon contact with a user's skin;
- an electrically conductive underlayer disposed under the sensor base and electrically coupled thereto;
- a circuit layer disposed under the underlayer and electrically coupled to the sensor via the underlayer;
- a first elastic layer overlying at least a portion of the sensor base and arranged so as to be disposed adjacent the sensor pad and extending therearound; and
- a second elastic layer disposed under the circuit layer.

* * * * *